US010261038B2

(12) United States Patent
Kost et al.

(10) Patent No.: US 10,261,038 B2
(45) Date of Patent: Apr. 16, 2019

(54) TIRE INSPECTION APPARATUS (71) Applicant: Bridgestone Bandag, LLC, Muscatine, IA (US)

(72) Inventors: Troy A. Kost, LeClaire, IA (US); Eric M. Henriksen, Muscatine, IA (US); Christopher J. A. Ferrell, Bettendorf, IA (US)

(73) Assignee: Bridgestone Bandag, LLC, Muscatine, IA (US)

(*) Notice: Subject to any disclaimer, the term of this patent is extended or adjusted under 35 U.S.C. 154(b) by 0 days.

(21) Appl. No.: 15/540,036

(22) PCT Filed: Dec. 14, 2015

(86) PCT No.: PCT/US2015/065465
§ 371 (c)(1),
(2) Date: Jun. 27, 2017

(87) PCT Pub. No.: WO2016/109166
PCT Pub. Date: Jul. 7, 2016

(65) Prior Publication Data
US 2017/0363558 A1    Dec. 21, 2017

Related U.S. Application Data (60) Provisional application No. 62/098,044, filed on Dec. 30, 2014.

(51) Int. Cl.
*G01M 17/02* (2006.01)
*G01N 27/20* (2006.01)

(52) U.S. Cl.
CPC .......... *G01N 27/20* (2013.01); *G01M 17/022* (2013.01); *G01N 27/205* (2013.01)

(58) Field of Classification Search
CPC ... G01N 27/20; G01N 27/205; G01M 17/013; G01M 17/022
See application file for complete search history.

(56) References Cited

U.S. PATENT DOCUMENTS

| 1,779,907 A | 10/1930 | Dye |
| 3,465,242 A | 9/1969 | Gruetzmacher et al. |

(Continued)

FOREIGN PATENT DOCUMENTS

| CN | 201229313 | 4/2009 |
| CN | 101614689 | 12/2009 |
| GB | 2395791 | 6/2004 |

OTHER PUBLICATIONS

Retread with Hawkinson, Hawkinson Website, visited on May 31, 2014.

(Continued)

*Primary Examiner* — Noam Reisner (57) ABSTRACT

A tire inspecting apparatus for a tire is provided. The apparatus includes a test stand for supporting and rotating a tire. The test stand is configured such that a tire supported thereon defines a center axis. The apparatus includes a testing probe configured as a high voltage electrode for generating an electric field and a grounding element. A positioning assembly includes a support bracket and a positioning arm supporting the testing probe. The positioning arm is operable to move the testing probe into a working position between the sidewalls of a tire supported on the test stand and in proximity to the grounding element. The positioning arm is connected to the support bracket for pivoting movement relative to the support bracket about a pivot axis. The pivot axis extends at a non-perpendicular angle relative to the center axis of a tire supported on the test stand.

19 Claims, 7 Drawing Sheets (56) References Cited

U.S. PATENT DOCUMENTS

| | | | |
|---|---|---|---|
| 4,516,068 A | 5/1985 | Hawkinson, Jr. et al. | |
| 4,520,307 A | 5/1985 | Weiss | |
| 6,050,136 A | 4/2000 | Hawkinson et al. | |
| 6,304,090 B1 | 10/2001 | Weiss | |
| 6,600,326 B2 | 7/2003 | Weiss | |
| 6,837,102 B2 | 4/2005 | Weiss | |
| 6,907,777 B2 | 6/2005 | Weiss | |
| 7,826,192 B2 | 11/2010 | Sinnett et al. | |
| 8,733,160 B2 | 5/2014 | Range et al. | |
| 2004/0016293 A1* | 1/2004 | Weiss | G01M 17/02 73/146 |
| 2013/0162265 A1 | 6/2013 | Beccavin et al. | |
| 2013/0174657 A1 | 7/2013 | Beccavin et al. | |
| 2016/0167466 A1* | 6/2016 | Speyer | G01M 17/022 73/146.2 |

OTHER PUBLICATIONS

Lisa Lisle, Made in Maritimes How do they do that? How is a tire retreaded? The resurrection of a tire Moncto's ultra-modern Goodyear Retread Centre makes old tires as good as new, 25 percent cheaper than brand new ones, the Times, dated Oct. 20, 1995.
English Abstract of CN101614689, dated Dec. 30, 2009.
English Abstract of CN201229313, dated Apr. 29, 2009.
Bandag Retread System, undated, admitted prior art.

\* cited by examiner

TIRE INSPECTION APPARATUS

BACKGROUND OF THE INVENTION

Retreaded tires provide an economical way to gain additional use from tire casings after the original tread or retread has become worn. According to a conventional method of retreading, sometimes referred to as cold process retreading, worn tire tread on a used tire is removed to create a buffed, generally smooth treadless surface about the circumference of the tire casing to which a new layer of tread may be bonded. After the worn tire tread is removed, the tire casing is typically inspected for injuries, some of which may be skived and filled with a repair gum while others may be severe enough to warrant rejection of the casing.

After completion of the skiving process, the buffed surface may be sprayed with a tire cement that provides a tacky surface for application of bonding material and new tread. Next, a layer of cushion gum may be applied to the back, i.e., the inside surface of a new layer of tread, or alternatively, the layer of cushion gum may be applied directly to the tacky surface on the tire casing. Conventionally, the cushion gum is a layer of uncured rubber material. The cushion gum and new tread may be applied in combination about the circumference of the tire casing to create a retreaded tire assembly for curing. The cushion gum may form the bond between the tread and the tire casing during curing. Following assembly of the tire casing, cement, cushion gum and tread, the overall retreaded tire assembly may be placed within a flexible rubber envelope. The entire envelope tire assembly may be placed within a curing chamber and subjected to a vulcanization process that binds the materials together.

Several different methods may be used to perform the inspection of the used tire casing prior to application of the new tread. One method may be a visual inspection. A visual inspection typically involves an inspector visually observing the tire casing as it rotates on a test stand. While a visual inspection may be useful for detecting large flaws in used tire casings, many tire defects, such as small or obscure holes, are difficult to detect in a visual inspection. Moreover, visual inspections can be slow and time consuming. If flaws are overlooked during the inspection, it may lead to a defective retreaded tire.

Other tire inspection methods involve the use of a testing head or probe that carries a high voltage. The probe is applied to the interior surfaces of a tire being tested while a corresponding grounding element, which may be part of a tire spreader or tire rotating device, is applied to the outside of the tire opposite the probe. Defects are detected by arcing between the testing head and the grounding element through the defect.

With such testing devices, the probe is generally supported on the end of a mechanical arm that can be used to help manipulate the probe between the beads of the tire casing and into the interior of the tire casing. However, the mechanical arms used to move the probes can still make it difficult to maneuver the probe into the proper position inside the tire casing. In many cases, despite the use of the adjustable arm, operator intervention may be required to help the probe pass between the beads of the tire casing and into the interior of the tire casing. This can make the inspection process more time consuming and increase the chance that the probe is positioned incorrectly in the tire casing. Additionally, many mechanical arms used with high voltage testing probes are not easily adapted to different sized and/or configured tires. As a result, a large number of different mechanical arms may be necessary for different tire sizes or the mechanical arm may require a large number of adjustments to accommodate tires of different sizes. In either case, it results in a more time consuming and cumbersome inspection process.

BRIEF SUMMARY OF THE INVENTION

The invention provides a tire inspecting apparatus for a tire having a pair of sidewalls and an outer wall spanning the sidewalls. The tire inspecting apparatus includes a test stand for supporting and rotating a tire with the test stand being configured such that a tire supported thereon defines a center axis. The tire inspecting apparatus includes a testing probe configured as a high voltage electrode for generating an electric field and a grounding element. A positioning assembly includes a support bracket; and a positioning arm supporting the testing probe. The positioning arm is moveable between extended and retracted positions in a telescoping manner. The positioning arm is operable to move the testing probe into a working position between the sidewalls of a tire supported on the test stand and in proximity to the grounding element. The positioning arm is connected to the support bracket for pivoting movement relative to the support bracket about a pivot axis. The pivot axis extends at a non-perpendicular angle relative to the center axis of a tire supported on the test stand.

In another aspect, the invention provides a positioning assembly for manipulating a testing probe relative to a tire having a center axis. The positioning assembly includes a support bracket and a positioning arm supporting the testing probe and movable between extended and retracted positions in a telescoping manner. The positioning arm is connected to the support bracket for pivoting movement relative to the support bracket about a pivot axis with the pivot axis extending at a non-perpendicular angle relative to the center axis. The positioning assembly is configured such that the testing probe is movable by the positioning arm between an idle position wherein the testing probe is outside of the tire and the positioning arm is in the retracted position, a first intermediate position wherein the testing probe is at least partially outside of the tire and the positioning arm is in the retracted position and pivoted about the pivot axis relative to the support bracket as compared to the idle position, a second intermediate position wherein the testing probe is positioned inside of a pair of planes each defined by a respective one of the sidewalls of the tire and the positioning arm is in the extended position, and a working position wherein the testing probe is positioned between the sidewalls of the tire and the positioning arm is pivoted on the about the pivot axis relative to the support bracket as compared to the idle position.

According to a further aspect, the invention provides a testing probe for sensing defects in a tire when arranged in proximity of a grounding element. The testing probe includes a mount including a connecting portion configured to connect to an arm and a supporting portion that extends at a non-perpendicular angle relative to the connecting portion. A head is attached to the supporting portion of the mount. The head is configured such that the position of the head relative to the mount is adjustable. A plurality of wire loops are attached to the head and configured to fan out from at least three sides of the head.

DETAILED DESCRIPTION OF THE INVENTION

Figure 1:
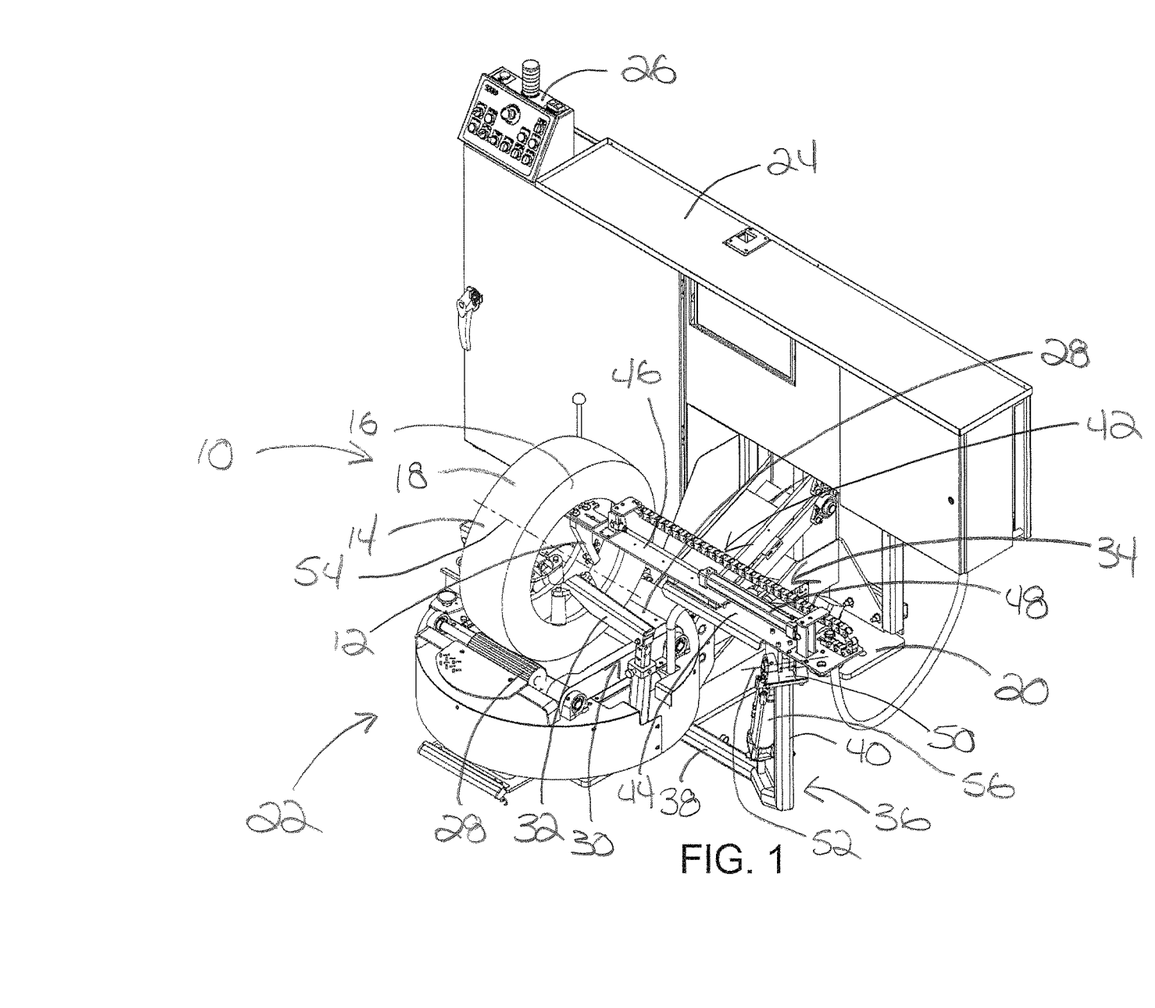
FIG. 1 is a perspective view of an exemplary view of a tire inspection apparatus according to the present invention.
Figure 2:
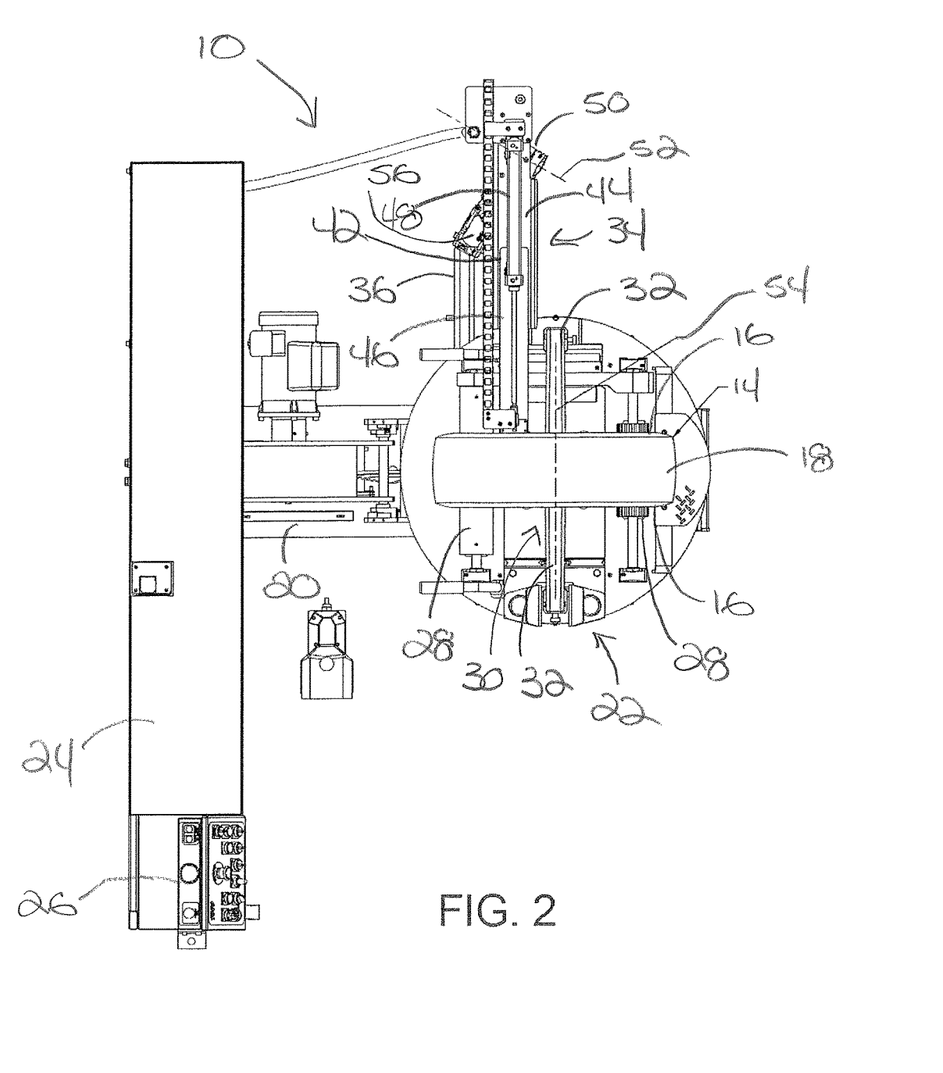
FIG. 2 is a top view of the tire inspection apparatus of FIG. 1

Referring to FIGS. 1-2 of the drawings there is shown an illustrative tire inspection apparatus 10 constructed in accordance with the present invention. The illustrated tire inspection apparatus 10 is operable to scan the interior liner of a tire or tire casing using a testing probe 12 to detect defects in the tire casing such as holes and embedded nails. The testing probe 12 may be configured as a high voltage electrode that generates an electrical field in close proximity to the inner liner of the tire casing. When a grounding element is applied to the side of the tire opposite the testing probe, a defect in the tire casing can be detected by electrical arcing between the testing probe and the grounding element through the defect in the tire.

In the illustrated embodiment, a tire casing 14 that is being inspected as part of a retreading process is shown mounted on the tire inspection apparatus 10. The illustrated tire casing 14 is a buffed tire casing that generally includes a pair of side walls 16 bounded by a generally radially outer wall 18 or crown that spans side walls 16. Each side wall 16 extends radially inward from outer wall 18 and terminates in a bead area designed for mounting on the tire rim (not shown). After the tire tread wears beyond a certain limit, a tire must either be discarded or retreaded before it should be used on the vehicle for which it was designed. In a retreading process, the remaining used tire tread is removed from the tire casing by a buffing machine. Next, the tire casing is inspected for any holes, nicks or tears due to stones or other sharp objects the tire comes in contact with during use. This inspection may be performed, at least in part, using the tire inspection apparatus 10 shown in FIGS. 1-2. After the inspection is completed, any injured or damaged area may be repaired prior to the application of the new tire tread to the tire casing.

While aspects of the tire inspection apparatus 10 of the present invention is described in the context of an inspection performed as part of a tire retreading process, those skilled in the art will appreciate that use of the tire inspection apparatus 10 is not limited to such applications. In particular, the tire inspection apparatus 10 could be used in any application in which a tire or tire casing is inspected for damage. Moreover, the tire inspection apparatus 10 of the invention is not limited to use with buffed tire casings and is equally applicable to other forms of tires including tires with an attached tread.

In the illustrated embodiment, the tire inspection apparatus 10 generally includes a base 20 that supports a test stand 22, an electrical enclosure 24 and an operator station 26. The electrical enclosure 24 may house various electrical components associated with operation of the tire inspection apparatus 10. These components may include a high voltage power source in communication with the testing probe 12 for providing high voltage electricity to the testing probe 12. The components may further include one or more control systems that may direct operation of one or more operating components of the tire inspection apparatus 10 as well as to provide information to an operator, such as through the operator station 26, regarding the inspection process and results. The operator station 26 may otherwise include controls that can be used an operation to direct the inspection process.

As shown in FIGS. 1 and 2, the test stand 22 may include a pair of spaced apart rollers 28 for supporting the tire casing 14. The rollers 28 may be connected to a suitable motor to allow the rollers to rotate the tire casing about its center axis. One or both of the rollers 28 may be connected to an electrical ground so as to define a grounding element for the testing probe 12. The test stand 22 may be configured to move in an upward or downward direction relative to the base 20.

In order to facilitate insertion of the testing probe 12 into the interior of the tire casing 14, the test stand 22 may include a tire spreader 30 that is operable to spread the beads of the tire casing 14 apart. As shown best shown in FIG. 1, the tire spreader 30 may include two opposed retractable arms 32 each having a pair of downwardly extending rollers. To spread the beads of a tire casing apart, the rollers of each arm may be inserted into the interior of the tire and brought into engagement with a respective one of the tire beads. The arms 32 may then be retracted to pull the beads away from each other thereby providing a larger opening into the interior of the tire casing 14. As will be appreciated, the present invention may be configured in such a manner that a tire spreader is unnecessary.

For moving the testing probe 12 into the interior of the tire casing, the tire inspection apparatus 10 may include a positioning assembly 34 that is supported on a rigid support bracket 36. In the illustrated embodiment as shown in FIGS. 1 and 2, the support bracket 36 may have a generally L-shaped configuration including a horizontal first portion 38 that connects to the test stand 22 and a vertical or upright second portion 40 that extends in perpendicular relation relative to the first portion 38. The positioning assembly 34 may include a telescoping positioning arm 42 having a free end on which the testing probe 12 is supported. The positioning arm 42 may include a stationary portion 44 that is supported on the rigid support bracket 36 and an extendable portion 46 on which the testing probe 12 is supported. The extendable portion 46 of the positioning arm 42 may be supported on the stationary portion 44 of the positioning arm 42 in such a manner that allows the extendable portion 46 to extend and retract in a longitudinal direction with respect to the stationary portion 44. For driving this telescoping movement, the positioning arm 42 may include a linear actuator 48 that is connected on one end to the stationary portion 44 of the arm and at the other end to the extendable portion 46 of the arm. With this arrangement, extension and retraction of the linear actuator 48 extends and retracts the extendable portion 46 of the arm thereby moving the testing probe 12 inwards and outwards relative to the stationary portion 44 of the arm and the support bracket 36.

To provide for further movement of the positioning arm 42, the arm may be pivotally connected to the support bracket 36. To this end, as best shown in FIGS. 1 and 2, the positioning arm 42 may be supported on the upright portion 40 of the support bracket 36 by a pivot joint 50 that has a pivot axis 52 that extends at a non-perpendicular angle relative to the center axis 54 of a tire casing 14 supported on the test stand 22. For driving pivotal movement of the positioning arm 42 relative to the support bracket 36, the positioning assembly 34 may include a pivot actuator 56 that, as shown in FIG. 1, has one end attached to the horizontal portion 38 of the support bracket 36 and a second end attached to the positioning arm 42 such that extension and retraction of the pivot actuator 56 causes the positioning arm 42 to pivot about the pivot axis 52 relative to the support bracket 36 and, in turn, the test stand 22 and the tire casing 14 supported on the test stand 22.

Figure 3:
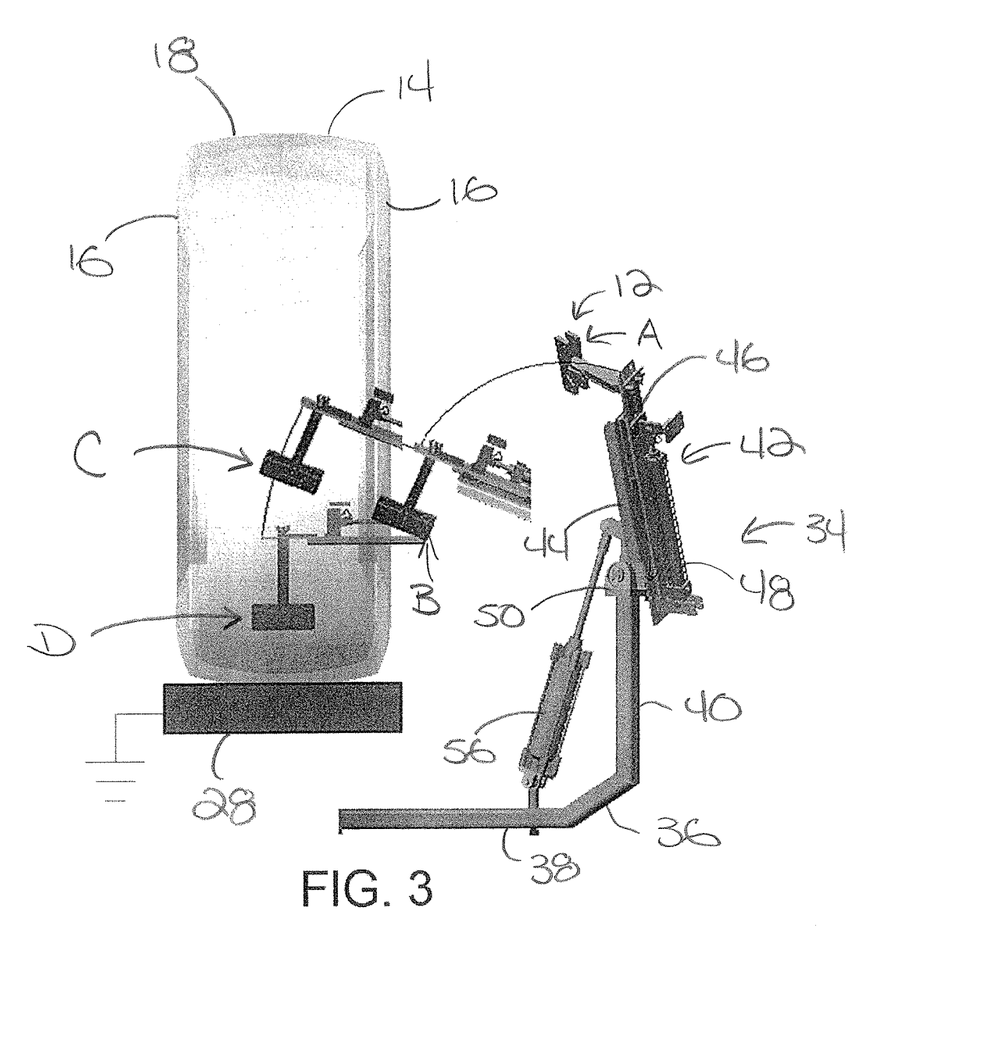
FIG. 3 is a schematic end view of the probe positioning arm of the tire inspection apparatus of FIG. 1 showing the movement of the positioning arm between the retracted position and the inserted position with respect to a tire casing.

For inserting the testing probe 12 into a tire casing 14 supported on the test stand 22, the positioning assembly 34 may be adapted to move the testing probe 12 in a multi-stage manner between a retracted or idle position in which the testing probe 12 is arranged away from the test stand 22 and an inserted or working position in which the testing probe 12 is arranged in the interior and adjacent the inner liner of a tire casing 14 supported on the test stand 22. The various stages of movement of the positioning arm 42 are shown in FIG. 3. In the idle position (referenced as A in FIG. 3), the positioning arm 42 extends generally upward and the extendable portion 46 is in the retracted position. In this position, the testing probe 12 and positioning arm 42 are spaced relatively far apart from the test stand 22 to facilitate removal and/or installation of a tire casing from the test stand. To move the testing probe 12 to the inserted or working position, the pivot actuator 56 first pivots the positioning arm 42 downward to a first intermediate position (referenced as B in FIG. 3) in which the testing probe 12 is outside of the tire casing 14 and above the lower portion of the rim of the tire casing 14 defined by the bead. In this first intermediate position, the testing probe 12 may be completely outside or partially inside of a plane defined by the edge of the bead on the side of the tire casing from which the positioning arm 42 is approaching. However, the testing probe 12 is not positioned completely inside of the tire casing in the first intermediate position.

Next, the positioning assembly 34 may move the testing probe 12 to a second intermediate position (referenced as C in FIG. 3) in which the testing probe 12 is arranged completely inside the tire casing 14 (e.g. between planes defined by the sidewalls of the tire casing) but still above the lower portion of the bead of the tire casing as shown in FIG. 3. In other words, the testing probe 12 may be arranged within a cylinder the size of the bead opening of the tire casing generally in line with the tire axis. The positioning arm 42 may move to this second intermediate position by extending the extendable portion 46 of the arm via operation of the linear actuator 48. After the testing probe 12 reaches the second intermediate position, it can then be moved to the inserted or working position (referenced as D in FIG. 3) in which testing probe 12 is arranged between the sidewalls 16 of the tire casing 14 and adjacent the inner liner thereof. Moreover, the testing probe 12 is opposite one of the rollers 28, which may be grounded. The testing probe 12 is shown in this working position in FIGS. 1 and 2. To reach the working position, the positioning assembly 34 pivots the positioning arm 42 further about the pivot axis 52, in this case in the downward direction, via operation of the pivot actuator 56 thereby moving the testing probe 12 between the beads of the tire casing 14 and into the space between the sidewalls 16. In operation, the positioning assembly 34 holds the testing probe 12 stationary in the working position while the tire casing 14 rotates past the testing probe 12.

Figure 4:
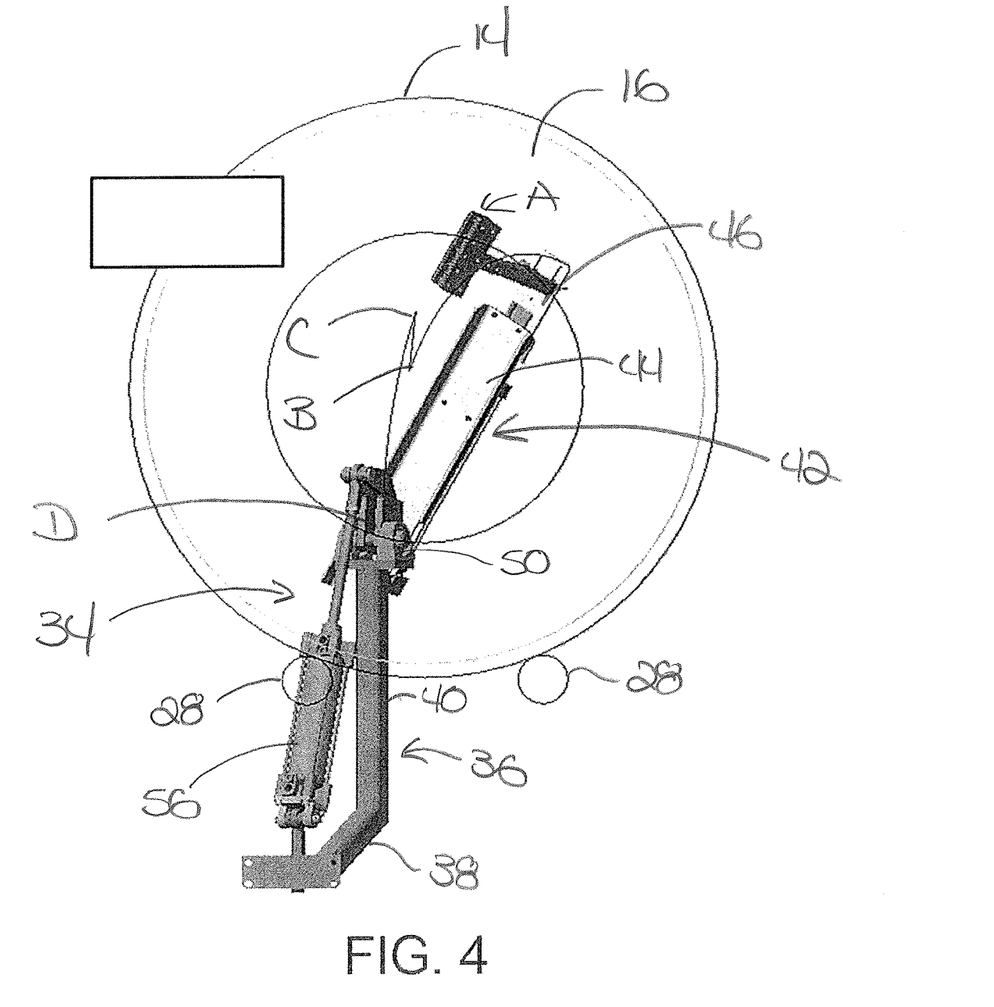
FIG. 4 is a schematic end view of the probe positioning arm of the tire inspection apparatus of FIG. 1 showing the movement path of the positioning arm with respect to a tire casing.

In the illustrated embodiment, the testing probe 12 is behind the centerline of the tire casing when in the working position, i.e. the testing probe 12 is positioned at an angle of less than 180° (more particularly, between 90° and 180°) with respect to the circumference of the tire casing as viewed from the side on which the positioning assembly 34 is arranged. The approximate path of the end of the positioning arm 42 as it moves between the idle, first intermediate, second intermediate and working positions (again referenced respectively as A, B, C, and D) is shown in FIG. 4.

These steps may be reversed to remove the testing probe 12 from the working position inside the tire casing 14. First, the testing probe 12 may be pivoted upward from the working position to the second intermediate position by pivoting the positioning arm 42 about the pivot axis 52 using the pivot actuator 56. Next, the testing probe 12 may be moved from the second intermediate position to the first intermediate position by retracting the extendable portion 46 of the arm using the linear actuator 48. The testing probe 12 may then be pivoted further upward from the first intermediate position to the idle position, again around the pivot axis 52, through operation of the pivot actuator 56.

The angled orientation of the pivot axis 52 with respect to the center axis 54 of the tire casing 14 and the multi-stage movement of the positioning arm 42 provides several advantages over existing positioning arms for high voltage testing probes. In particular, they allow the testing probe 12 to clear the hole in the tire across a larger range of tire sizes. Additionally, they allow the testing probe 12 to move into the area between the sidewalls 16 of the tire casing 14 without catching on the beads. Existing positioning arms drop the probe straight into the tire and often require an operator to help maneuver the probe past the beads and into the space between the sidewalls of the tire.

Figure 5:
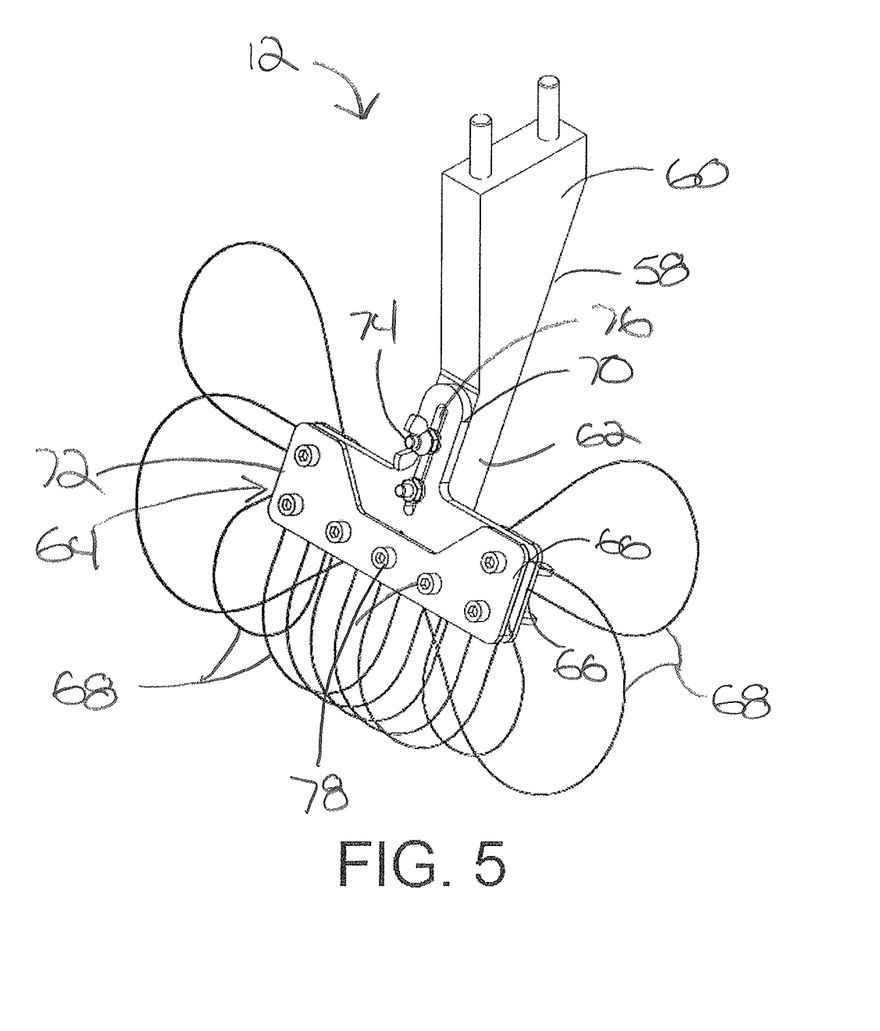
FIG. 5 is a perspective view of an exemplary high voltage testing probe according to the invention for use with the tire inspection apparatus of FIG. 1
Figure 6:
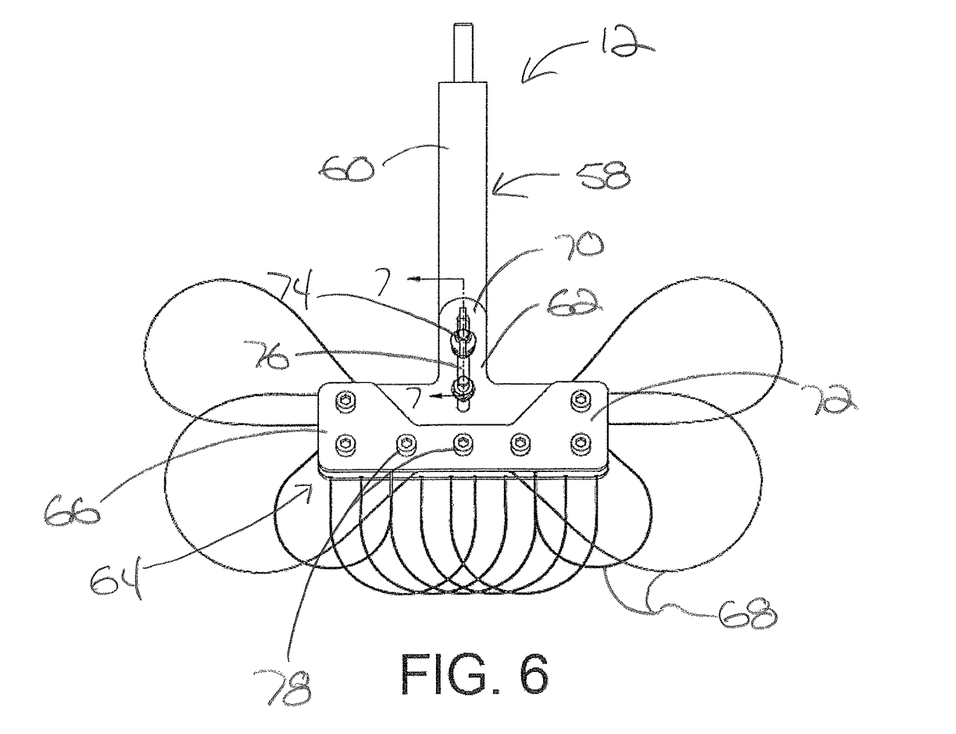
FIG. 6 is a plan view of the high voltage testing probe of FIG. 5.
Figure 7:
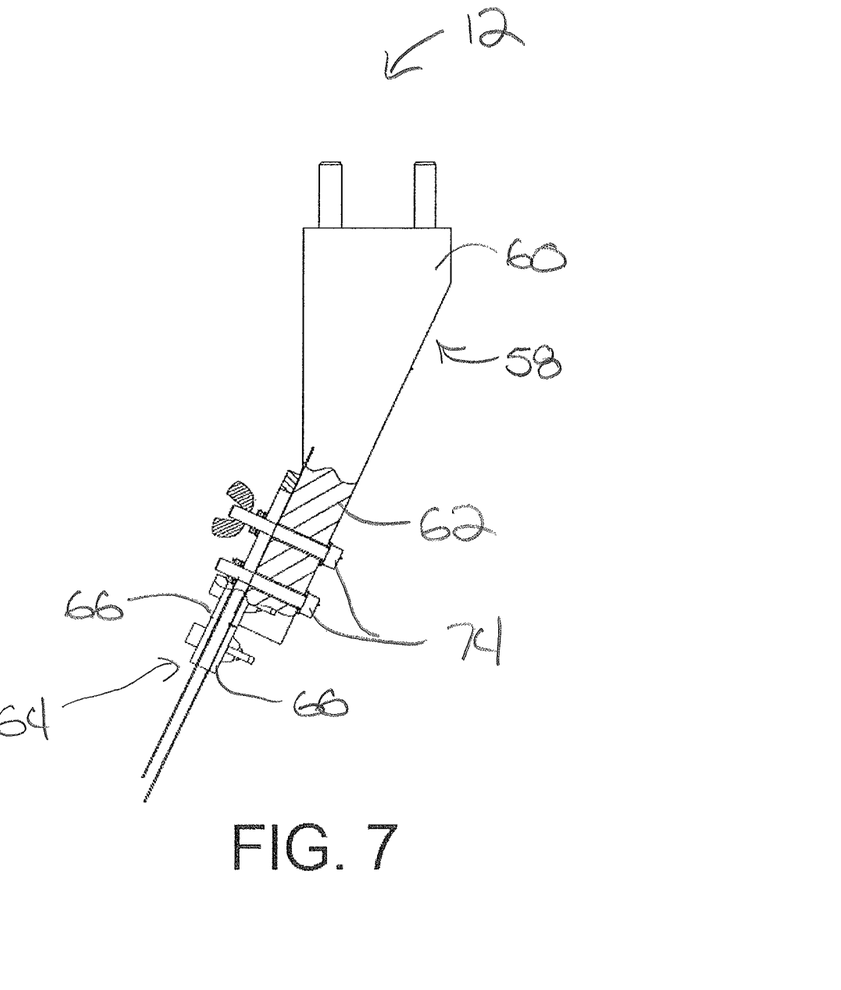
FIG. 7 is a side sectional view of the high voltage testing probe of FIG. 5

Referring to FIGS. 5-7 of the drawings there is shown an exemplary embodiment of the testing probe 12 that may be manipulated by the positioning assembly 34 into the inserted or working position with respect to a tire casing. In the illustrated embodiment, the testing probe 12 may include a mount 58 that may be made of an insulating material. As best shown in FIGS. 5 and 7, the mount 58 may have a connecting portion 60 at one end thereof that is configured for connection to the positioning arm 42 and supporting portion 62 at the other end thereof that extends at a non-perpendicular angle with respect to the connecting portion and, in turn, the longitudinal axis of the positioning arm 42. A head 64 may be connected to a distal end of the supporting portion 62 of the mount 58. As a result of the angled configuration of the mount 58, the head 64 extends at an angle relative to the longitudinal axis of the positioning arm 42.

The head 64 may include a pair of plates 66 arranged in an overlapping relationship with a plurality of electrically conductive wire loops 68 arranged therebetween. The plates 66 may be made of an electrically conducting material. Additionally, the head 64 may have a substantially T-shaped configuration including a base section 70 and a cross member 72 that extends perpendicularly relative to the base section 70. The base section 70 may attach to the supporting portion 62 of the mount 58 via one or more bolts 74 that are inserted through a slotted opening 76 in the base section 70. The slotted opening 76 may extend in the lengthwise direction of the base section 70 and perpendicular relative to the cross member 72. The size and T-shaped configuration of the head 64 allows it to fit inside between the sidewalls of a tire casing. Furthermore, the head 64 may be easily adjusted to accommodate tires of different shapes and sizes. For example, the position and orientation of the plates 66 may be adjusted simply by changing the position at which the head 64 connects to the mount 58 via the slotted opening 76 thereby changing the distance that the head 64 extends away from the mount 58. With such adjustments the testing probe 12 can be made to work with almost any shape or size tire.

The wire loops 68 may be configured and attached to the plates 66 (such as by fasteners 78) so as to fan out from the head 64 and be able to come into contact with the inner liner of a tire casing. In particular, the wire loops 68 may be configured and attached to fan out from both the end of the head 64 and the lateral sides of the head 64. The wire loops 68 may be selectively connectable to the high voltage power source contained within the electrical enclosure. Those skilled in the art will appreciate that other conductive flexible structures configured for contacting the inner liner of the tire could be used in place of the wire loops.

In operation, the testing probe 12 may be moved into the interior of the tire casing 14 by the positioning assembly 34 into the working position opposite one of the grounded rollers 28 after the tire casing has been placed on the test stand 22. The wire loops 68 attached to the head 64 of the testing probe 12 then may be connected to the high voltage power supply so as to create an electric field in the area around the testing probe 12. When inserted in the tire casing, this electrical field will produce an electric arc that connects the wire loops 68 of the testing probe 12 to the grounded roller 28 upon detection of a flaw, such as a hole, nail or other object, in the tire casing.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A tire inspecting apparatus for a tire having a pair of sidewalls and an outer wall spanning the sidewalls, the tire inspecting apparatus comprising:
   a test stand for supporting and rotating a tire, the test stand being configured such that a tire supported thereon includes a center axis, the center axis being perpendicular to the pair of sidewalls and parallel to the outer wall;
   a testing probe configured as a high voltage electrode for generating an electric field;
   a grounding element comprising a roller in contact with an outer wall of the tire, the roller supporting the tire on the test stand;
   a positioning assembly comprising:
   a support bracket; and
   a positioning arm supporting the testing probe, the positioning arm being moveable between extended and retracted positions in a telescoping manner, the positioning arm being operable to move the testing probe into a working position between the sidewalls of a tire supported on the test stand and in proximity to the grounding element, the positioning arm being connected to the support bracket for pivoting movement relative to the support bracket about a pivot axis, the pivot axis extending at a non-perpendicular angle relative to the center axis of a tire supported on the test stand.

2. The tire inspecting apparatus of claim 1 wherein the positioning assembly is configured such that the testing probe is movable by the positioning arm between an idle position wherein the testing probe is outside of a tire supported on the test stand and the positioning arm is in the retracted position, a first intermediate position wherein the testing probe is at least partially outside of a tire supported on the test stand and the positioning arm is in the retracted position and pivoted about the pivot axis relative to the support bracket as compared to the idle position, a second intermediate position wherein the testing probe is positioned inside of a pair of planes each defined by a respective one of the sidewalls of a tire supported on the test stand and the positioning arm is in the extended position, and the working position wherein the positioning arm is pivoted about the pivot axis relative to the support bracket as compared to the idle position.

3. The tire inspecting apparatus according to claim 2 wherein the positioning assembly includes a linear actuator for moving the positioning arm between the extended and retracted positions.

4. The tire inspecting apparatus according to claim 2 wherein the positioning assembly includes a pivot actuator for pivoting the positioning arm about the pivot axis.

5. The tire inspecting apparatus according to claim 1 wherein the support bracket includes a first portion connecting to the test stand and a second upright portion that extends in perpendicular relation to the first portion and wherein the positioning arm is connected to the second upright portion of the positioning arm.

6. The tire inspecting apparatus according to claim 1 wherein the testing probe includes a mount including a connecting portion configured to connect to the positioning arm and a supporting portion that extends at a non-perpendicular angle relative to the connecting portion and a head attached to the supporting portion of the mount.

7. The tire inspecting apparatus according to claim 6 wherein the head is configured such that the position of the head relative to the mount is adjustable.

8. The tire inspecting apparatus according to claim 7 wherein the position of the head relative to the mount is adjustable using a slotted opening in the head that receives a fastener that connects to the mount.

9. The tire inspecting apparatus according to claim 6 further including a plurality of wire loops attached to the head and configured to fan out from at least three sides of the head.

10. A positioning assembly for manipulating a testing probe relative to a tire having a center axis, the center axis being perpendicular to a pair of sidewalls of the tired and parallel to an outer wall of the tire, the positioning assembly comprising:
a support bracket; and
a positioning arm supporting the testing probe and movable between extended and retracted positions in a telescoping manner, the positioning arm being connected to the support bracket for pivoting movement relative to the support bracket about a pivot axis, the pivot axis extending at a non-perpendicular angle relative to the center axis;
wherein the positioning assembly is configured such that the testing probe is movable by the positioning arm between an idle position wherein the testing probe is outside of the tire and the positioning arm is in the retracted position, a first intermediate position wherein the testing probe is at least partially outside of the tire and the positioning arm is in the retracted position and pivoted about the pivot axis relative to the support bracket as compared to the idle position, a second intermediate position wherein the testing probe is positioned inside of a pair of planes each defined by a respective one of the sidewalls of the tire and the positioning arm is in the extended position, and a working position wherein the testing probe is positioned between the sidewalls of the tire and the testing probe is positioned coplanar with a roller in contact with an outer wall of the tire,
and the positioning arm is pivoted on the about the pivot axis relative to the support bracket as compared to the idle position.

11. The positioning assembly according to claim 10 further including a linear actuator for moving the positioning arm between the extended and retracted positions.

12. The positioning assembly according to claim 10 further including a pivot actuator for pivoting the positioning arm about the pivot axis.

13. The positioning assembly according to claim 10 wherein the support bracket includes a first portion and a second upright portion that extends in perpendicular relation to the first portion.

14. The positioning assembly according to claim 13 wherein the positioning arm is connected to the second upright portion of the positioning arm.

15. A testing probe for sensing defects in a tire when arranged in proximity of a grounding element, the tire having a pair of sidewalls and an outer wall spanning the sidewalls, the testing probe comprising:
a mount including a connecting portion configured to connect to an arm and a supporting portion that extends at a non-perpendicular angle relative to the connecting portion, the connecting portion being parallel to the pair of sidewalls and perpendicular to the outer wall;
a head attached to the supporting portion of the mount, the head being configured such that the position of the head relative to the mount is adjustable; and
a plurality of wire loops attached to the head and configured to fan out from at least three sides of the head, the plurality of wire loops configured to produce an electric arc with a roller of the grounding element, the roller in contact with an outer wall of the tire.

16. The testing probe according to claim 15 wherein the position of the head relative to the mount is adjustable using a slotted opening in the head that receives a fastener that connects to the mount.

17. The testing probe according to claim 15 wherein the head has a T-shaped configuration including a base section that connects to the supporting portion of the mount and a cross member that extends perpendicularly relative to the base section.

18. The testing probe according to claim 17 wherein the wire loops are attached to the cross member of the head.

19. The testing probe according to claim 15 wherein the head comprises a pair of plates arranged in overlapping relation.

* * * * *

UNITED STATES PATENT AND TRADEMARK OFFICE
CERTIFICATE OF CORRECTION

PATENT NO. : 10,261,038 B2
APPLICATION NO. : 15/540036
DATED : April 16, 2019
INVENTOR(S) : Kost et al.

It is certified that error appears in the above-identified patent and that said Letters Patent is hereby corrected as shown below:

In the Claims

In Column 9, Line 25, delete "tired" and insert -- tire --.

Signed and Sealed this
Twenty-fourth Day of March, 2020

Andrei Iancu
*Director of the United States Patent and Trademark Office*